United States Patent
Naeymi-Rad et al.

(10) Patent No.: US 11,817,191 B1
(45) Date of Patent: Nov. 14, 2023

(54) SYSTEM AND METHODS FOR DISPLAYING GENOMIC AND CLINICAL INFORMATION

(71) Applicant: Leap of Faith Technologies, Inc., Libertyville, IL (US)

(72) Inventors: Frank Naeymi-Rad, Libertyville, IL (US); Barbara Rapchak, Batavia, IL (US)

(73) Assignee: Leap of Faith Technologies, Inc., Libertyville, IL (US)

( * ) Notice: Subject to any disclaimer, the term of this patent is extended or adjusted under 35 U.S.C. 154(b) by 79 days.

(21) Appl. No.: 17/144,348

(22) Filed: Jan. 8, 2021

Related U.S. Application Data (60) Provisional application No. 63/092,919, filed on Oct. 16, 2020, provisional application No. 62/960,028, filed on Jan. 12, 2020.

(51) Int. Cl.
| | |
|---|---|
| *G16H 10/60* | (2018.01) |
| *G06N 3/126* | (2023.01) |
| *G06F 16/248* | (2019.01) |
| *G06F 3/0482* | (2013.01) |

(52) U.S. Cl.
CPC ........... *G16H 10/60* (2018.01); *G06F 3/0482* (2013.01); *G06F 16/248* (2019.01); *G06N 3/126* (2013.01)

(58) Field of Classification Search
CPC ..... G16H 10/60; G06F 3/0482; G06F 16/248; G06N 3/126
See application file for complete search history.

(56) References Cited

U.S. PATENT DOCUMENTS

| | | |
|---|---|---|
| 5,799,268 A | 8/1998 | Boguraev |
| 5,930,788 A | 7/1999 | Wical |
| 6,055,540 A | 4/2000 | Snow |
| 6,101,515 A | 8/2000 | Wical et al. |
| 6,904,432 B2 | 6/2005 | Charlot et al. |
| 7,167,858 B2 | 1/2007 | Naeymi-Rad et al. |
| 7,496,593 B2 | 2/2009 | Gardner et al. |
| 7,536,387 B2 | 5/2009 | Charlot et al. |
| 7,693,917 B2 | 4/2010 | Charlot et al. |

(Continued)

OTHER PUBLICATIONS

JinMing Huang et al., "Using knowledge Graphs to Enhance the Interpretability of Clinical Decision Support Model," 2020 International Conference on Computer Science and Management Technology (ICCSMT), IEEE, Nov. 2020, pp. 115-122. (Year: 2020).*

(Continued)

*Primary Examiner* — Dino Kujundzic
(74) *Attorney, Agent, or Firm* — Lathrop GPM LLP; Richard Beem; Alex Shtraym (57) ABSTRACT

The present invention relates to a system and methods for displaying genomic and clinical information. More specifically, the invention is directed to a system for collecting, displaying, and modeling an individual's genomic makeup, physiological characteristics, healthcare history, and lifestyle to enable personalized medicine, better understand the transition from health to disease, and identify additional risk factors for disease. Certain embodiments of the system facilitate generating and displaying a patient record on a graphical user interface. Additionally, embodiments of the invention allow users through the use of user interface to annotate, augment, and overall interact with the clinically more accurate and detailed user interface.

15 Claims, 11 Drawing Sheets

(56) References Cited

U.S. PATENT DOCUMENTS

| | | | |
|---|---|---|---|
| 7,711,671 | B2 | 5/2010 | Meyers |
| 7,870,117 | B1 | 1/2011 | Rennison |
| 8,589,400 | B2 | 11/2013 | Naeymi-Rad et al. |
| 9,940,266 | B2 | 4/2018 | Van Rooyen et al. |
| 10,092,213 | B2 * | 10/2018 | Gossler .................. G16H 30/20 |
| 10,678,876 | B1 * | 6/2020 | Young .................... G16H 40/63 |
| 11,145,395 | B1 * | 10/2021 | Mitchell ................ G16H 40/67 |
| 2003/0045782 | A1 | 3/2003 | Iliff |
| 2003/0140063 | A1 * | 7/2003 | Pizzorno ................. G16Z 99/00 |
| 2005/0158767 | A1 * | 7/2005 | Haskell .................. G16B 20/20 |
| | | | 702/20 |
| 2005/0240572 | A1 | 10/2005 | Sung et al. |
| 2005/0283387 | A1 * | 12/2005 | Donoghue ............. G16H 70/20 |
| | | | 705/2 |
| 2007/0179776 | A1 | 8/2007 | Segond et al. |
| 2008/0065452 | A1 | 3/2008 | Naeymi-Rad et al. |
| 2009/0083231 | A1 | 3/2009 | Eberholst et al. |
| 2009/0254572 | A1 | 10/2009 | Redlich et al. |
| 2010/0169299 | A1 | 7/2010 | Pollara |
| 2010/0179827 | A1 * | 7/2010 | McCallie, Jr. ......... G16H 50/70 |
| | | | 707/E17.014 |
| 2010/0262659 | A1 | 10/2010 | Christiansen et al. |
| 2010/0324936 | A1 | 12/2010 | Vishnubhatla et al. |
| 2011/0112866 | A1 | 5/2011 | Gerrans |
| 2011/0184960 | A1 | 7/2011 | Delpha et al. |
| 2011/0231786 | A1 * | 9/2011 | Kenney .................. G16H 10/60 |
| | | | 715/771 |
| 2011/0301982 | A1 | 12/2011 | Green, Jr. et al. |
| 2012/0166525 | A1 | 6/2012 | Dittrich |
| 2012/0179696 | A1 | 7/2012 | Charlot et al. |
| 2013/0191165 | A1 * | 7/2013 | MacDonald ........... G16H 15/00 |
| | | | 705/3 |
| 2013/0268290 | A1 * | 10/2013 | Jackson ................. G16B 50/10 |
| | | | 705/2 |
| 2013/0325493 | A1 * | 12/2013 | Wong ...................... G16Z 99/00 |
| | | | 705/2 |
| 2014/0032125 | A1 * | 1/2014 | Hawkins ................ G16B 50/00 |
| | | | 702/19 |
| 2015/0089365 | A1 * | 3/2015 | Zhao ...................... G16H 10/60 |
| | | | 715/708 |
| 2015/0187228 | A1 * | 7/2015 | Boguski ................. G16H 20/10 |
| | | | 434/262 |
| 2015/0356250 | A1 * | 12/2015 | Polimeni ................ G16H 10/60 |
| | | | 705/3 |
| 2016/0188836 | A1 * | 6/2016 | Stopek .................... G06F 16/22 |
| | | | 705/3 |
| 2016/0247170 | A1 * | 8/2016 | Soulakis ................. G16H 50/30 |
| 2016/0283667 | A1 * | 9/2016 | Rachapalli ............. G16H 10/60 |
| 2019/0206531 | A1 * | 7/2019 | Vandersluis ........... G16H 30/40 |
| 2019/0355447 | A1 * | 11/2019 | Barkol .................. G06F 3/0484 |
| 2020/0286630 | A1 * | 9/2020 | Takahata ................ G16H 10/60 |
| 2020/0319770 | A1 * | 10/2020 | Varga ..................... G16H 40/63 |
| 2021/0065914 | A1 * | 3/2021 | Martinez ................ G16H 10/60 |
| 2021/0090694 | A1 * | 3/2021 | Colley ................... G16B 40/00 |
| 2021/0124465 | A1 * | 4/2021 | Sahu ...................... G06F 3/0482 |
| 2021/0313077 | A1 * | 10/2021 | Smurro .................. G16H 50/20 |

OTHER PUBLICATIONS

Anthony Masi et al., "Developing a Search Algorithm and a Visualization Tool for SNOMED CT," (IJACSA) International Journal of Advanced Computer Science and Applications, vol. 6, No. 4, 2015, pp. 19-23. (Year: 2015).*

"Semantic Web: Asking the Right Questions", Duch et al., Seventh International Conference on Information and Management Sciences, Urumchi, China, Aug. 12-19, 2008 entire document www.fizyka.umk.pl/ftp/pub/papers/kmk/08-SemWeb.pdf.

"Social tagging overview (SharePoint Server 2010)" May 12, 2010 entire document http://technet.microsoft.com/en-us/library/ff608137.aspx.

Bronnert, et al., Problem-Centered Care Delivery, Journal of AHIMA 83, No. 7 (Jul. 2012): 30-35.

Trace, et al. Testing Pattern Recognition as a Method for Measuring Severity of Illness. SCAMC, Inc. 1989 (5 pages).

Naeymi-Rad. A Feature Dictionary to Support Database Translation, Information Retrieval, Intelligent Medical Records, and Expert Systems. Doctoral Thesis. (135 pages).

Durand. Accelerating Informatics Innovation. Alphachimp. GACS Explainer Video Storyboard. Dated Aug. 26, 2019.

* cited by examiner

SYSTEM AND METHODS FOR DISPLAYING GENOMIC AND CLINICAL INFORMATION

CROSS-REFERENCE TO RELATED APPLICATIONS

This application claims benefit of U.S. Application No. 63/092,919 filed on Oct. 16, 2020 and U.S. Application No. 62/960,028 filed on Jan. 12, 2020, each of which is incorporated by reference in its entirety.

FIELD OF THE INVENTION

This invention relates to the field of medical informatics, and more particularly to a system and methods for displaying genomic and clinical information.

BACKGROUND

Conventional medical informatics systems are in widespread use in a variety of clinical and pharmacy settings. Examples of such systems include personal health records (PHR), pharmacy information system (PIS), electronic health record (EHR), and electronic medical record (EMR).

These conventional systems typically include a collection of electronically stored information about a patient's medical history. EHRs may contain a broad range of data, including demographics, medical history, medication history, allergies, immunization records, laboratory test results, radiology images, vital signs, personal characteristics like age and weight, and billing information. Many commercial EHR systems combine data from a number of healthcare services and providers, such as clinical care facilities, laboratories, radiology centers, and pharmacies.

Conventional systems may also use a scoring system, such an Apache Physiology and Chronic Health Evaluation (APACHE), for classifying a disease. Typically, this includes measuring certain physiological measurements for use with other medical data and certain baseline health information related to a patient.

However, genomics data is difficult to access through conventional systems. Genomic datasets require a large amount of resources, such as memory. An individual's genome and their microbiome can be hundreds of gigabytes in size. When extrapolated over large populations, the data can reach petabytes or exabytes in size.

Also, differing standards between bioinformatics and clinical informatics of conventional systems create a barrier between data and medical professionals. Sequencing labs provide only a snippet of unstructured genomic data in a file format that the conventional systems may not be able to use.

Medical professionals and patients alike need to be able to access this wealth of data and understand how to interpret and act upon it. Knowledge of who is most at risk of developing a disease, coupled with the ability to detect the onset of a disease in its earliest stage, could enable early intervention to prevent or cure the disease.

Advances in medicine have increased life expectancy, yet patients typically don't receive care until they fall ill, at which point the standard of care is to treat the disease, not the patient. Healthcare costs are on the rise across most countries, yet according to the World Health Organization, about 20-40% of spending is wasted in part due to providing treatment to non-responders. Although cancer incidence and prevalence are increasing at an alarming rate, progress in treatment has been slow, and treatment benefits are measured in weeks to months.

Therefore, there is a need for a system and methods for collecting, displaying, and modeling an individual's genomic makeup, physiological characteristics, healthcare history, and lifestyle to enable personalized medicine, better understand the transition from health to disease, and identify additional risk factors for disease. The present invention satisfies this demand.

SUMMARY

Briefly, a user interface for a medical informatics system may display medical data including information regarding a patient's genome, diagnoses, and prescribed treatment.

The user interface may display a virtual representation of a patient (e.g., anatomical feature or pathology) including one or more graphical components. The virtual representation of a patient may depict highlighted elements (i.e. "hot spots") that correspond to a problem area associated with a patient's "problem list" compiled in the patient's medical record, personal health record (PHR), pharmacy information system (PIS), or other electronic health record (EHR).

The highlighted elements may collectively represent a history of medical diagnoses for a patient. Additionally or alternatively, the user interface may include a patient's medical history, such as prescribed medications. The highlighted elements may be mapped to the chromosomes, genes, and/or gene variants associated with the identified hot spot.

The highlighted elements may also be depicted using certain colors interface to indicate the severity of, for example, a patient's condition in specific areas. For example, red may be used to represent a severe problem in a hot spot. In certain embodiments, clinical codes may be used to map the information stored in the medical record to a virtual representation, or to an actual medical image (e.g., X-ray, CT, MRI, and ultrasound images) of the patient.

The user interface may depict one or more graphical components as a network of "nodes", or "clusters" where each node is an interactive element that may be selected to obtain additional information, either specific to the patient or non-personalized reference information from a database. A graphical component may be shown as a clinical data cluster and associate with clinical data of a patient. Additionally or alternatively, a graphical component may be shown as a genomic data cluster and associate with genomic data of a patient. It is further contemplated that graphical components may associate also with generalized information accessible to the system.

A user may access additional information about a highlighted area through use of an input device, such as a cursor or through use of a touchscreen. Additional information related to the selected area may be displayed including: a date, medical diagnoses, clinical procedures, prescribed treatment, prescribed medications, associated clinical and administrative codes, affected chromosome, gene, gene variant, and reference data.

More detailed information on any item in the displayed list may be accessed by selecting the individual item. In addition, a user may accessed additional information about a diagnosis, medication, or treatment through use of an input device to link to the patient's PHR, PIS, EHR or other health record.

A computer system for creating a virtual representation of a patient medical record may comprise a processor and a main memory in communication with the processor via a communication infrastructure, said memory including stored instructions that, when executed by said processor, cause said processor to: receive a patient medical record including clinical data and genomic data and create a structured data set; analyze the structured data set, wherein the structured data set identifies a region of interest corresponding to an anatomical feature and/or pathology; generate the virtual representation of the patient medical record based on the structured data set, the virtual representation including one or more graphical components associated with the region of interest; and display the virtual representation such that a user may interact with the one or more graphical components shown on the virtual representation. The processor may be configurable to permit selection of a graphical component such that information about the selected graphical component is accessed and displayed to a user.

A method for keeping, organizing and managing electronic records on at least one computer may comprise: generating a first instance of a plurality of data objects during a first encounter, said plurality of data objects comprising data elements further comprising a first instance identifier and temporal identifiers; linking a data object in said first instance to a summarization reference with a pointer, where the plurality of data objects and the summarization reference are related as part of a directed graph data structure; creating an additional instance of a plurality of data objects during a later encounter, said additional instance of a plurality of data objects comprising data elements further comprising an additional instance identifier and temporal identifier; providing continuity for said plurality of data objects of said first instance over time, wherein said providing step comprises tracking a relationship between said data object of said first instance and a data object of said additional instance; and generating a virtual representation of the electronic record, the virtual representation including genomic information and a body map.

While the invention is susceptible to various modifications and alternative forms, specific exemplary embodiments thereof have been shown by way of example in the drawings and have herein been described in detail. It should be understood, however, that there is no intent to limit the invention to the particular embodiments disclosed, but on the contrary, the intention is to cover all modifications, equivalents, and alternatives falling within the scope of the invention as defined by the appended claims.

BRIEF DESCRIPTION OF THE DRAWINGS

Embodiments are illustrated by way of example and not limitation in the figures in the accompanying drawings, in which like references indicate similar elements and in which.

DETAILED DESCRIPTION OF THE PREFERRED EMBODIMENTS

This invention relates to the field of medical informatics, and more particularly to a system and methods for generating and displaying a user interface of a patient medical record such that a user can annotate, augment, and overall interact with clinically more accurate and detailed medical information. Advantageously, the system is configured to collect, display, and model an individual's genomic makeup, health status, health history, and social determinants of health to enable personalized medicine, better understand the transition from health to disease, and identify additional risk factors for disease.

Figure 1:
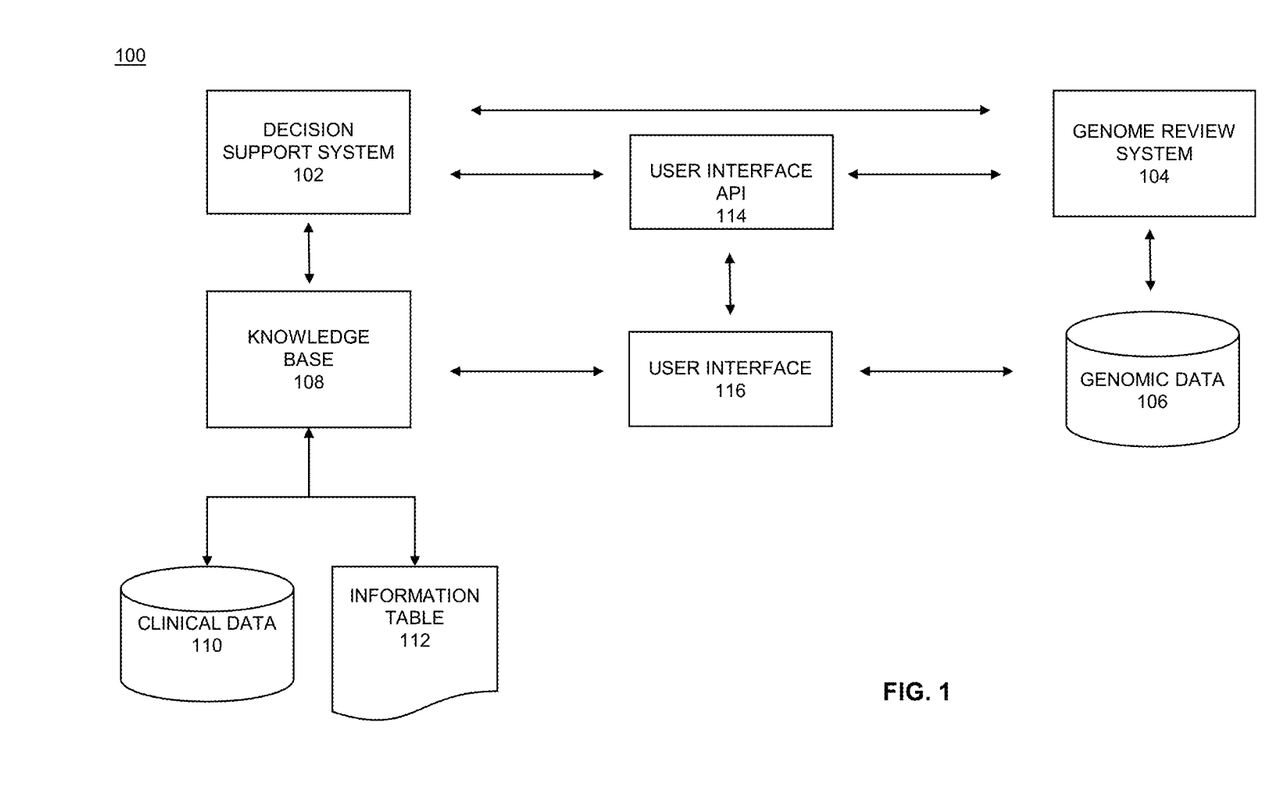
FIG. 1 illustrates a schematic diagram of an exemplary operation for generating and displaying a patient medical record.

Turning to the figures, FIG. 1 illustrates one embodiment of the system 100 for generating and displaying a user interface of a patient medical record. In the embodiment of the system illustrated in FIG. 1, a decision support system interoperates 102 with a genome review system 104. Genome review system 104 may retrieve genetic information (such as a patient's full genomic profile history) from a genomic database 106 (for example, a Genomic Archiving and Communication System) for display, review, and/or annotation.

While decision support system 102 and the genome review system 104 are shown as separate interoperating systems, it is contemplated that the decision support and the genome review functions are subsystem components of a single integrated system.

Decision support system 102 may create a structured data set from information provided by genome review system 104 and a knowledge base 108. Decision support system 102 may further be configured to manage workflow, execute rules, interface with external data, integrate with one or more EHRs, and more. In certain embodiments, decision support system 102 may integrate with an EHR via CDS Hooks and/or SMART-on-FHIR.

Knowledge base 108 may be configured to provide access to information about a specific patient and/or a clinical topic stored in a clinical data archive 110 or information table 112. For example, knowledge base 108 may access one or more EHRs and retrieve information from various health care providers. Also, knowledge base 108 may be configured to provide, for example, generalized information related to the medical condition and genome information from various resources accessible to system 100. Examples of and sources accessible to knowledge base 108 may include NCI Licensed treatments, NCCN, NCI PDQ, ClinVar, ClinGen, PharmVar, CPIC, PharmGKB, Cravat, The Cancer Genome Atlas, NCI Genomic Data Commons, OncoKB, CIViC, DGIdb, ClinicalTrials.gov.

Clinical data 108 may be stored in a format, such as Health Level-7 (HL7) or Fast Healthcare Interoperability Resources (FHIR), or translated into one of these formats before being stored and allocated within knowledge base 108 by resource code and ICD code. This information may then be used to support the creation of a user interface, as detailed below. System 100 may also use the information to generate and display data entry forms, diagrams, or other user interface elements.

In the Illustrated embodiment of system 100, the interaction between the decision support system 102 and the genome review system 104, and that which results from that interaction may be facilitated using a user interface applications program interface ("API") 114.

User interface API 114 may facilitate the bi-directional association of clinical data 108 and the information that may describe characteristics of anatomical features and pathologies of a patient provided through knowledge base 108 with genomic data 106 provided through genome review system 104.

A user interface 116 of system 100 may display a virtual representation of a patient (e.g., anatomical feature or pathology), descriptive components, graphical components, and temporal elements, as detailed below. The user interface may depict graphical components as a network of "nodes", or "clusters" where each node is an interactive element that may be selected to obtain additional information, either specific to the patient or non-personalized reference information from a database. More specifically, a graphical component may be shown as a genomic data cluster and associate with genomic data of a patient. In addition, a graphical component may be shown as a clinical data cluster and associate with clinical data of a patient. It is further contemplated that graphical components may associate with generalized information accessible to system 100.

The user interface may further display descriptive components, such as descriptive drawings, callouts, and captions that depict or describe a genome, anatomical feature and/or pathology as an overlay or modification on user interface 116.

Embodiments of system 100 may permit a user to interact with one or more interactive components of user interface 116 to retrieve, display, or record information about the clinical data and/or genomic data that are associated with these graphical components via the user interface. For instance, in response to a user input, system 100 may display a descriptive component including previously-recorded clinical data about the patient's condition, including allowing for recording, editing, and storage of this information. Examples of inputs that the system can receive include mouse clicks, typed text, touch, gestures, utterances, gaze data, image data.

System 100 may further be configured to display detailed information about the person's genome, highlighting genetic variations that may have implications for diagnosed diseases, conditions, treatments, and prescribed medications.

In certain embodiments, system 100 may facilitate using the clinical data associated with a genome, feature or pathology to display geometric properties of that feature. For example, certain patient characteristics may be stored in the knowledge base, which the system may use to generate one or more graphical components associated with those characteristics.

To facilitate the diagnosis and treatment of the patient, system 100 may access relevant bodies of information, such as Clinical Decision Support Guidelines and Acceptable Use Criteria. In certain embodiments of system 100, analysis of the relevant genomic data and clinical data may be performed wholly by a user, automatically, or a combination of both.

Furthermore, system 100 may conduct health topic searches, provide recommendations for patient care, provide hyperlinks to relevant products and resources, and the like. As should be apparent to one of ordinary skill in the art from the disclosure herein, other related services may also be provided.

Exemplary Flowcharts 200, 300

The exemplary flowcharts provided herein are for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

Figure 2:
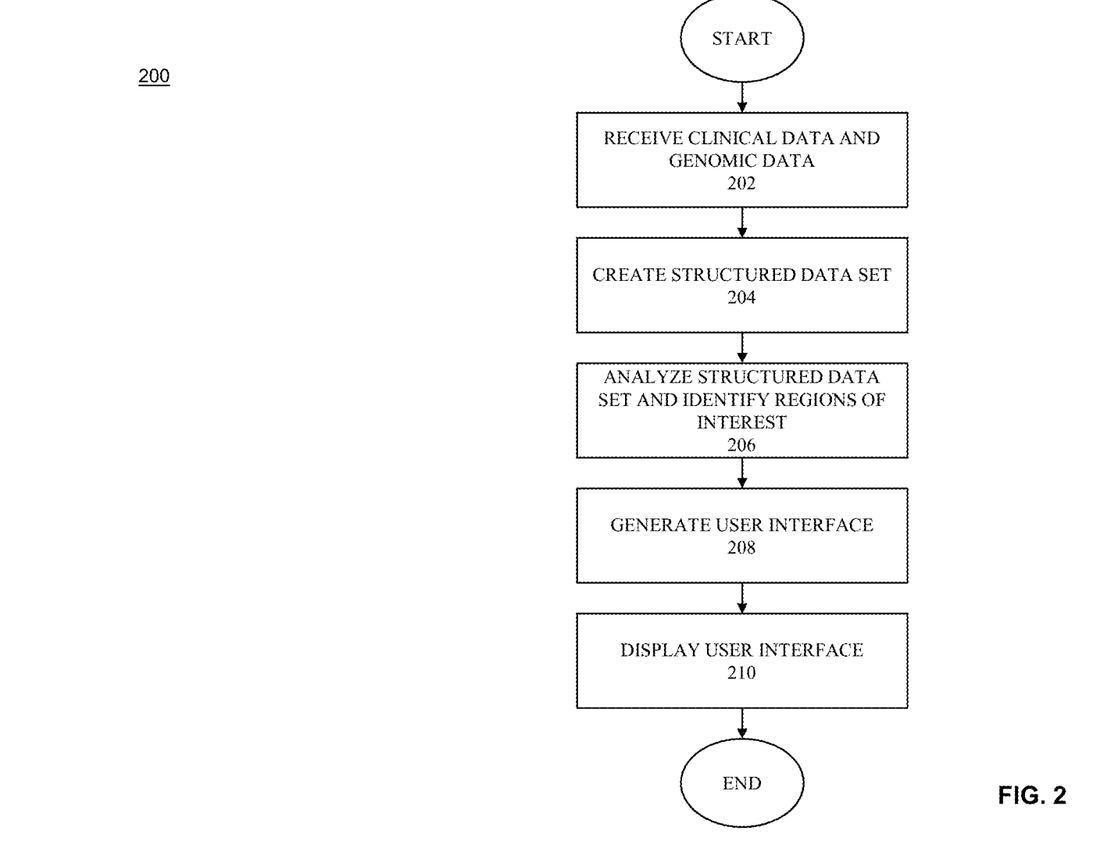
FIG. 2 is a flow chart illustrating an exemplary operation for generating and displaying a patient medical record.

FIG. 2 is a flow chart 200 illustrating an exemplary operation for generating a user interface of a patient medical record. As shown in FIG. 2, the operation begins, and at step 202, the system may receive a patient medical record, which may include clinical data and genomic data. In step 204, the system may create a structured data set based on the clinical data and genomic data. In step 206, the system may analyze the structured data set, and identify a region of interest corresponding to an anatomical feature and/or pathology. In step 208, the system may generate the user interface of the patient medical record based on the structured data set. The user interface may include a virtual representation of the patient and graphical components associated with the region of interest. In step 210, the system may then display user interface such that a user may interact with the one or more graphical components linked to the virtual representation.

Figure 3:
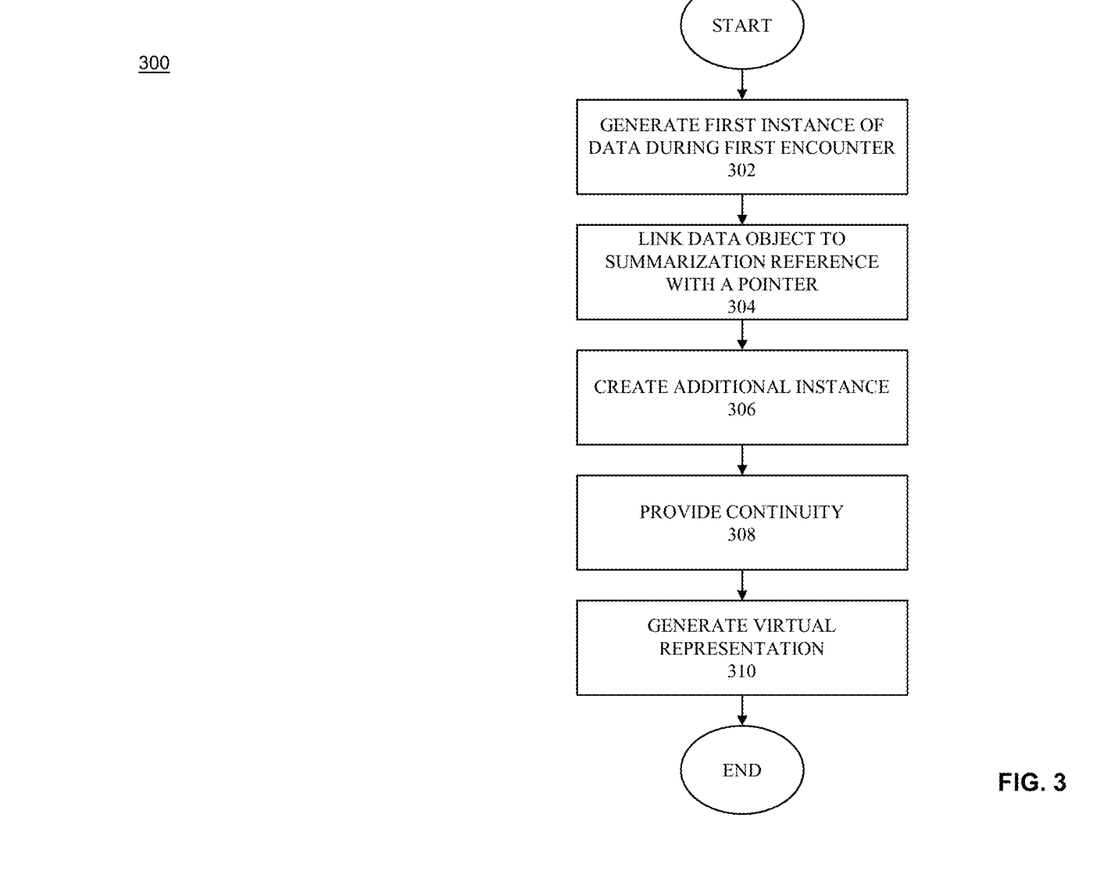
FIG. 3 is a flow chart illustrating an exemplary method for keeping, organizing, and managing electronic records.

FIG. 3 is a flow chart 300 illustrating an exemplary operation for keeping, organizing, and managing electronic records on at least one computer. As shown in FIG. 3, the operation begins and, in step 302, the system may generate a first instance of a plurality of data objects during a first encounter, said plurality of data objects comprising data elements further comprising a first instance identifier and temporal identifiers. In step 304, the system may link a data object in said first instance to a summarization reference with a pointer, where the plurality of data objects and the summarization reference are related as part of a directed graph data structure. In step 306, the system may create an additional instance of a plurality of data objects during a later encounter, said additional instance of a plurality of data objects comprising data elements further comprising an additional instance identifier and temporal identifier. In step 306, the system may provide continuity for said plurality of data objects of said first instance over time, wherein said providing step comprises tracking a relationship between said data object of said first instance and a data object of said additional instance. In step 310, the system may generate a user interface of the electronic record, the user interface including a virtual representation and graphical components associated with clinical information and genomic information.

User Interface 400

Figure 4:
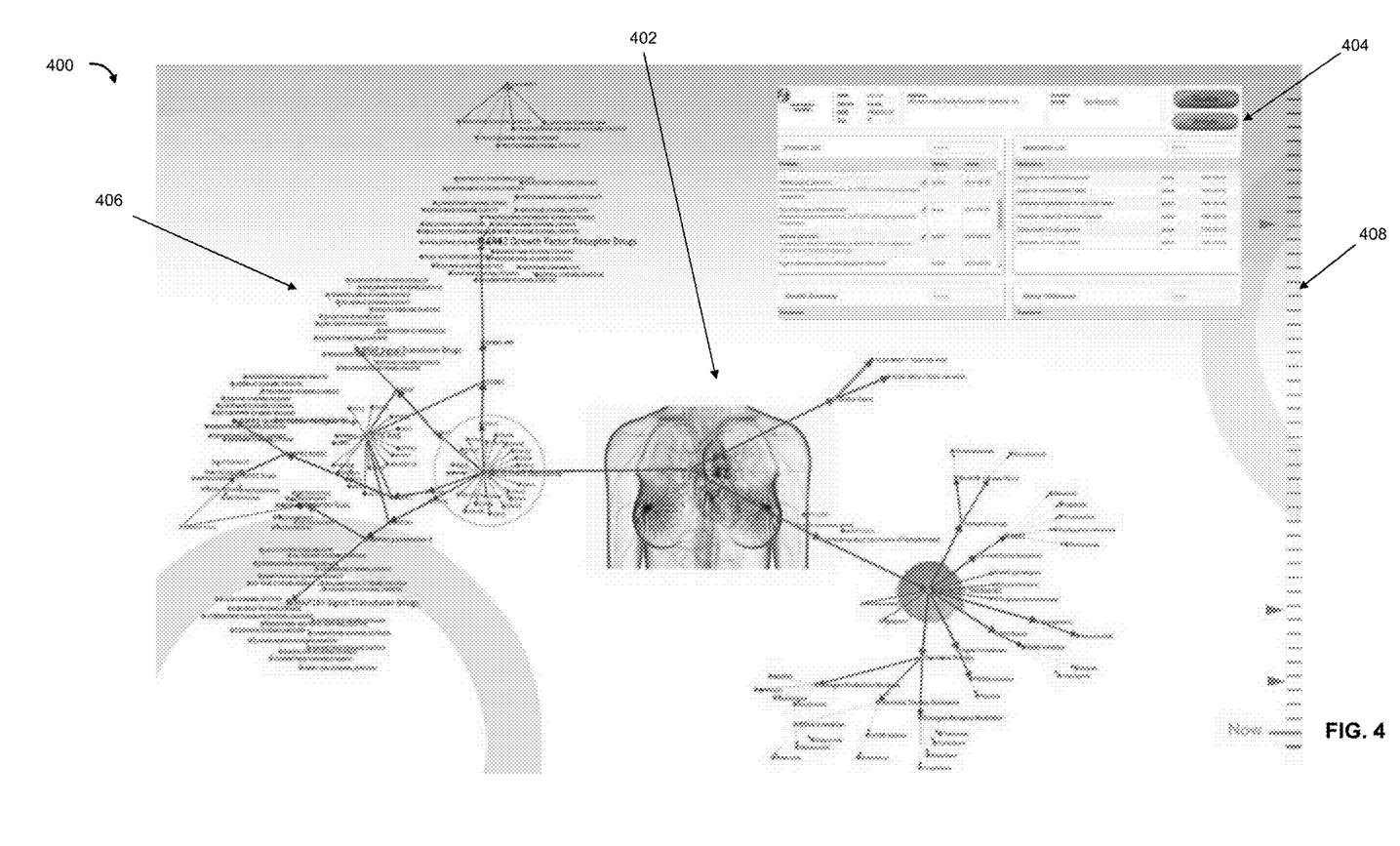
FIG. 4 is an exemplary user interface for displaying a patient medical record.

FIG. 4 illustrates an exemplary user interface 400 that a user may view and navigate. User interface 400 may incorporate iconography, drawings, callouts, and captions, the position and nature of which may be derived from the structured data set.

User interface 400 may display an individual's genomic makeup, health status, health history, and social determinants of health to enable personalized medicine, better understand the transition from health to disease, and identify additional risk factors for disease. In certain embodiments, user interface 400 may display a plurality of problem areas and diagnoses for the selected patient.

User interface 400 may further include medical history specific to the individual patient and display this data as caption boxes, callout boxes, or iconography. In certain embodiments, user interface 400 may include prognosis information, such as based on the structured data set and/or the information from a knowledge base corresponding to the patient and specific topics.

In addition, user interface 400 may include and display optional treatment recommendations, such as based on the prognosis information or combined with the patient's medical history, genomic data, current medical status, or projected health status as of the date the information was compiled. In addition, user interface 400 may place the patient, anatomical feature, and/or pathology in a greater spatial and/or temporal, or "spatiotemporal" context, for example, before and after medical treatment.

In certain embodiments, user interface 400 can be used to automatically trigger the derivation (or retrieval) of analytical results based on recorded data about an anatomical feature or pathology, as well as display the resulting notifications. For example, the automatic display of the recommended treatment may be presented based on recorded data from given medical studies combined with clinical data and genomic data. In certain embodiments, by selecting a recommendation, notification or callout on user interface 400, a summary of the associated guideline and the supporting patient data may be displayed.

As shown in FIG. 4, user interface 400 may include various interactive components to, for example, assist medical professionals with visualizing operational scenarios and identifying treatment options. Interactive elements may include a virtual representation 402 of the patient, descriptive elements 404 based on stored data corresponding to the patient, and graphical components 406 based on stored data corresponding to the patient, and temporal elements 408.

Virtual Representation 402

As shown, user interface 400 may include a virtual representation 402 (also referred to as a "body map"). Virtual representation 402 may include anatomical sketches or actual medical images (such as X-ray or MRI images) corresponding to the patient. By compiling long-term, longitudinal, clinical data with genomic data, the system may generate virtual representation 402 that considers both clinical and genomic parameters at a point in time, and compares them to the same parameters measured on previous dates, or to the same parameters in other individuals with similar profiles.

Through use of the user interface 400, a medical professional may view the patient's medical history as a body map including elements indicating significant events relative to specific body systems. The elements may collectively represent a codified problem list of medical diagnoses for a patient. The body map may further comprise a codified history of prescribed treatment, including medications. User interface 400 may provide the user with the ability to select elements on virtual representation 402, which may consist of information about the patient's genetic makeup, medical diagnoses, prescribed treatment for the patient, and the like.

In certain embodiments, user interface 400 may include hyperlink connections for connecting virtual representation 402 to one or more other virtual representations and/or structured data sets that are connected to associated data, related reports, relevant images or other similar pertinent clinical and/or genomic content to provide further efficient data entry or analysis.

Descriptive Components 404

Descriptive component 404 of user interface 400 may provide information recorded about the patient, such as from an EHR. As with other interactive components of user interface 400, descriptive component 404 may be automatically generated from knowledge base based on the structured data set, i.e., the clinical data and genomic data corresponding to a patient.

Figure 5:
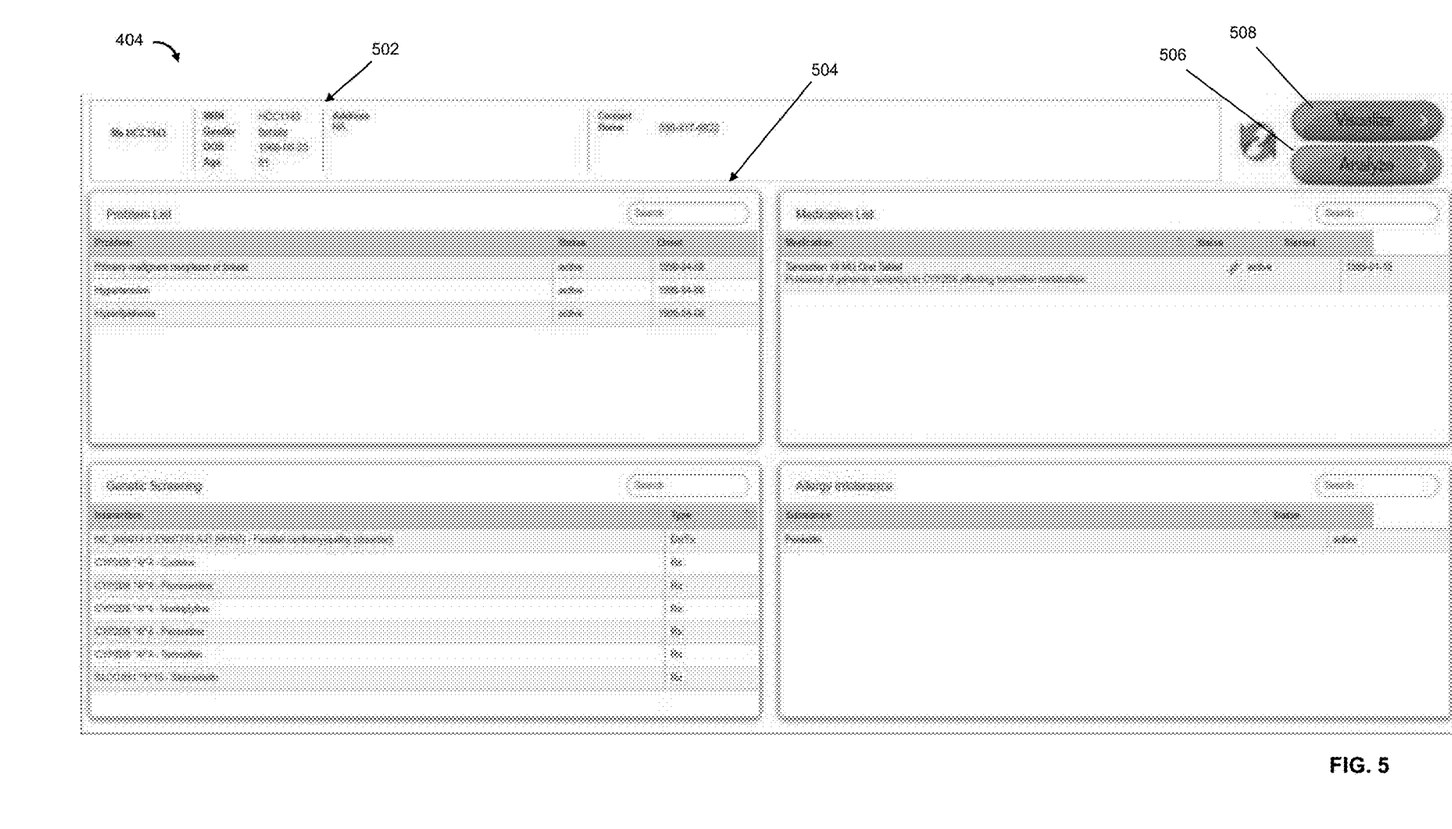
FIG. 5 illustrates an exemplary descriptive component of the user interface of FIG. 4.

As shown in FIG. 5, descriptive component 404 may include general information 502 about the patient, such as "MRN," "Gender," "DOB," "Age," "Address," and "Contact." In addition, descriptive component 404 may provide relevant medical information 504, such as "Problem List," "Medication List," "Genetic Screening," and "Allergy Intolerance."

Though use of descriptive component 404, for example, a user, such as a medical professional, may click on an "Analyze" button 506 to facilitate checking for genetic interactions on the problem list. A user may also click on a "Visualize" button 508 to facilitate displaying and/or updating visual representation 402 of the information shown in descriptive component 404.

In certain embodiments, an algorithm may determine the logical relevant history from the patient's problem list, and represent this by color coding a component on user interface 400 (for example, red for major problems, yellow for minor problems, and green for minor problems). The system may select items from the patient's problem list for placement on, for example, an anatomical feature or pathology of virtual representation 402 relevant to the diagnosis and treatment. In addition, the system may use a medical dictionary to include other body parts closely related to the current element. For example, if the element on the body map covers the heart, the medical dictionary may expand the body parts to include all significant diagnoses and treatment related to the cardiovascular system as a whole.

Descriptive component 404 may further include entry controls such as pick lists, checkboxes, numeric boxes, text boxes, and buttons, as well as mechanisms for displaying additional forms such as pop-ups, pop-overs, split/merges, and dissolve/replaces. Descriptive component 404 may also include data from pre-existing statistical analysis of probabilities and reliabilities of a combination of similar case-studies to the associated medical procedure and data associated with the patient's current health, genetic data, and medical history.

In certain embodiments, one or more items of descriptive component 404 may be emphasized (such as highlighted) to indicate significance. In addition, descriptive component 404 may include one or more symbols, such as a + symbol. For example, a user may use a cursor or touchscreen to select the + symbol to expand a column to display additional information. For example, the user may select the + to reveal additional clinical and/or administrative codes for the related item. Similarly, the user may select the + symbol to reveal coding equivalents for the medication (e.g. NDC codes).

Graphical Components 406

User interface 400 may further include graphical components 406 displayed as, for example, a plurality of nodes and indicated by a colored and/or numbered circle, that correspond to a one or more of a diagnosis, clinical code ICD-9, Medication prescribed, drug code RxNorm, drug Compliance, and/or Date related to the highlighted area of the patient's body. A graphical component may be shown as a genomic data cluster and associate with, for example, genomic data of a patient. In addition, a graphical component may be shown as a clinical data cluster and associate with clinical data of a patient. It is further contemplated that graphical components may associate also with generalized information accessible to the system.

A user may extract additional information about a graphical component through use of an input device or through use of a touchscreen or other sensitive display by touching the element. This additional information may be displayed in a "popup window" defined as an area of the screen that is superimposed over underlying information. The general purpose of the popup window relevant to the body map is to collectively present a quick, holistic view of significant medical diagnoses and related treatments for a specific area of the body to the user of the medical informatics system.

FIGS. 6-9 illustrate exemplary graphical components, which a user can interact with to, for example, initiate the retrieval and display of information relating to the patient's condition, diagnosis, and/or treatment options.

Figure 6:
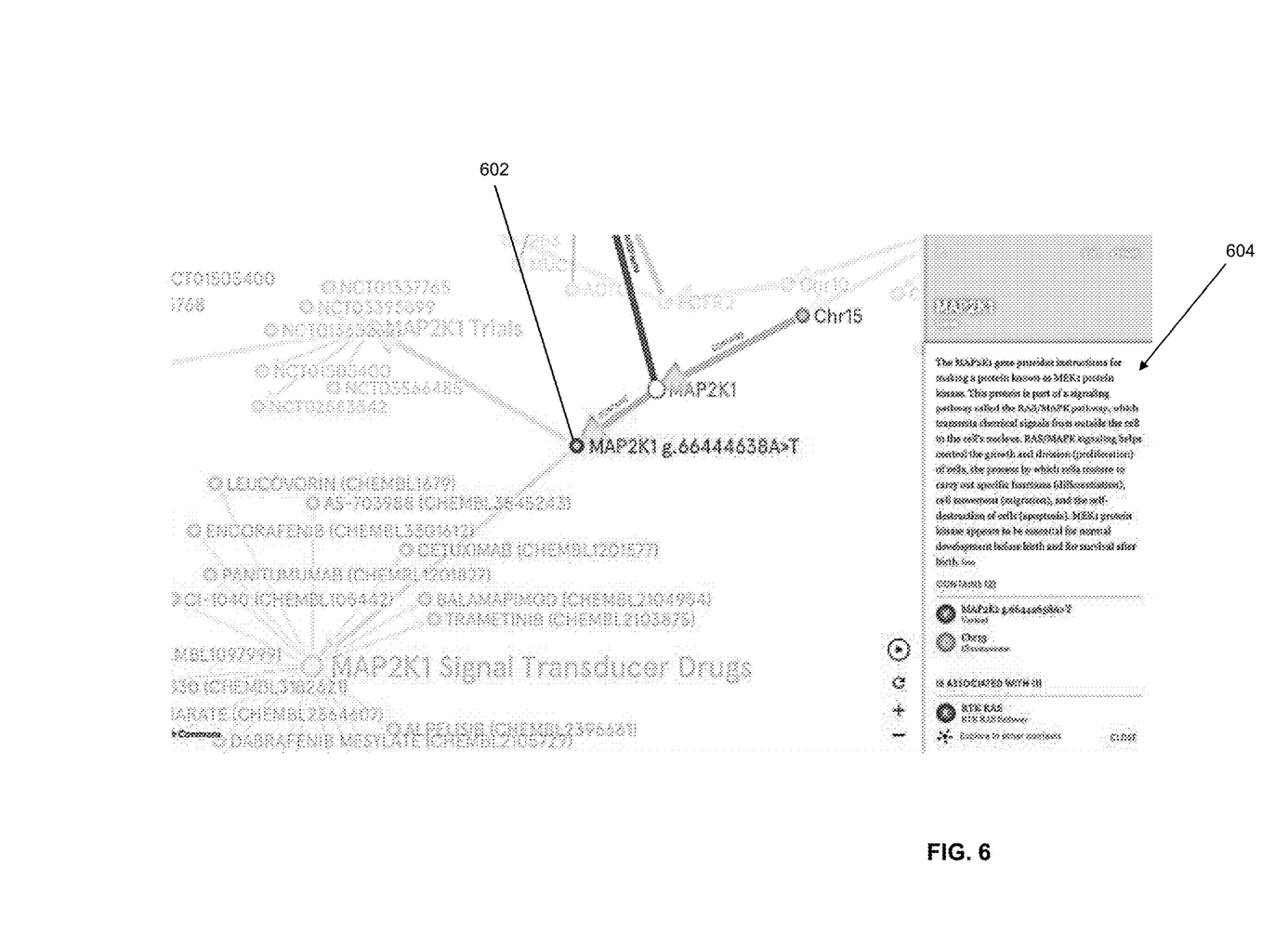
FIG. 6 illustrates an exemplary graphical component of the user interface of FIG. 4.
Figure 7:
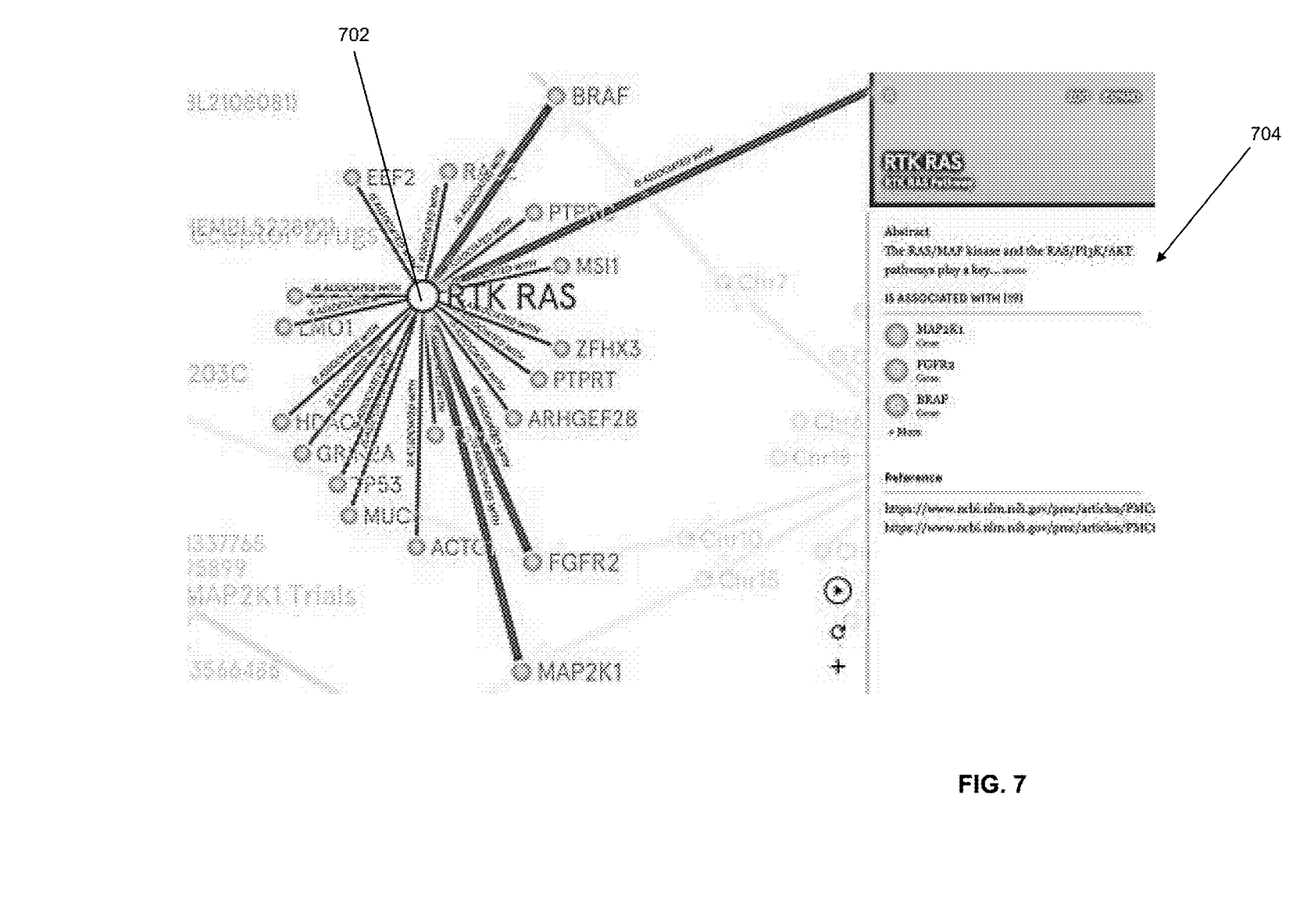
FIG. 7 illustrates another exemplary graphical component of the user interface of FIG. 4.

As shown in FIG. 6 and FIG. 7, detailed genomic Information can be obtained by clicking corresponding nodes to display detail and reference data. In particular, as shown in FIG. 6, when the node 602 for the MAP2K1 gene is clicked, detailed information 604 on the gene and the MAP2K1 gene variant is displayed, along with the RTK/RAS pathway. Furthermore, detail on the RTK/RAS pathway 702 can be displayed with links to references 704, as shown in FIG. 7.

Figure 8:
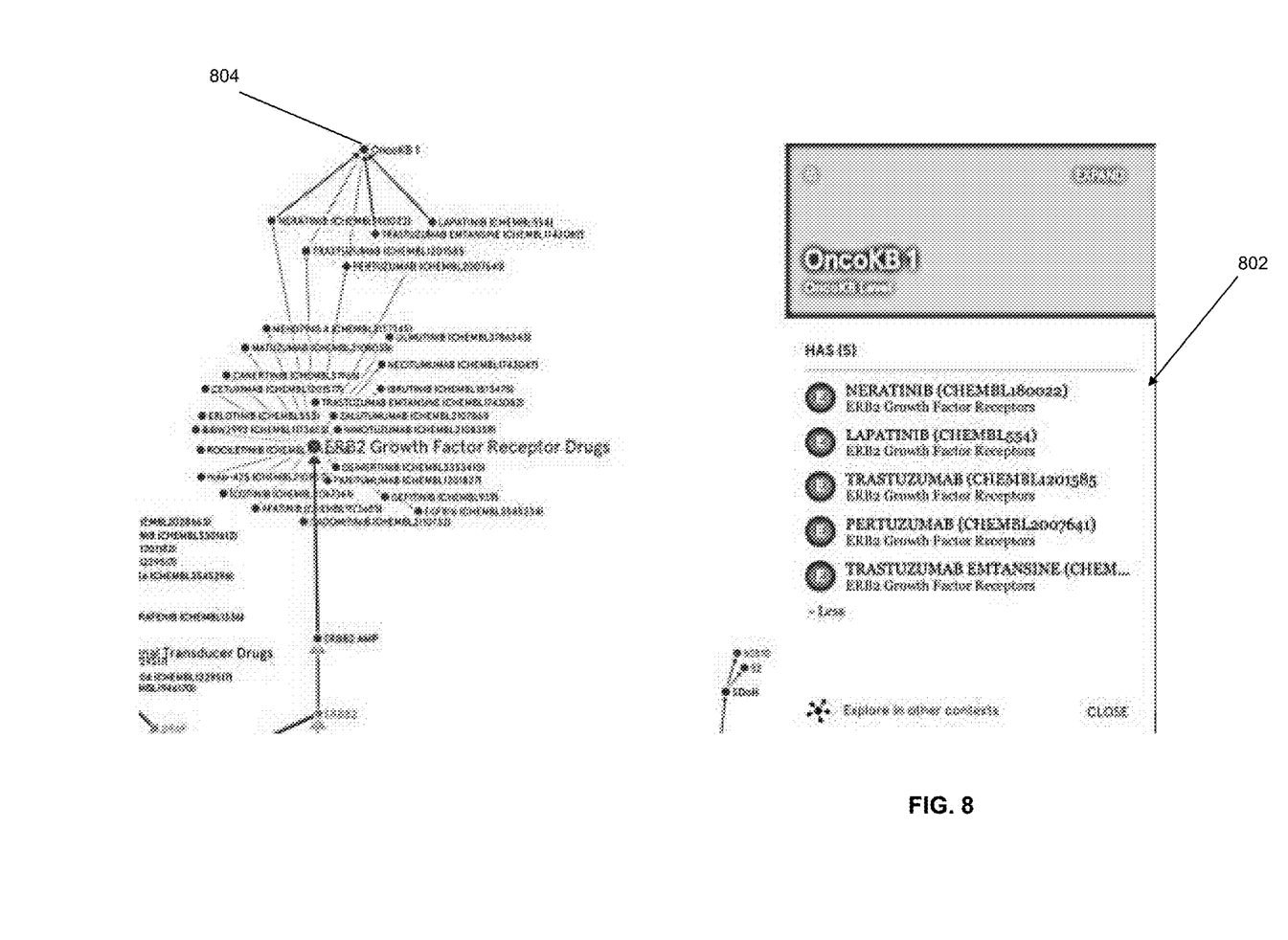
FIG. 8 illustrates another exemplary graphical component of the user interface of FIG. 4.

In addition, FDA-approved drugs relevant to the patient can be explored by clicking corresponding nodes. As shown in FIG. 8, detail 802 on OncoKB Level 1 drugs (those alterations which are FDA-recognized or considered standard care biomarkers predictive of response to FDA-approved drugs) is readily available by clicking the corresponding node 804.

Figure 9:
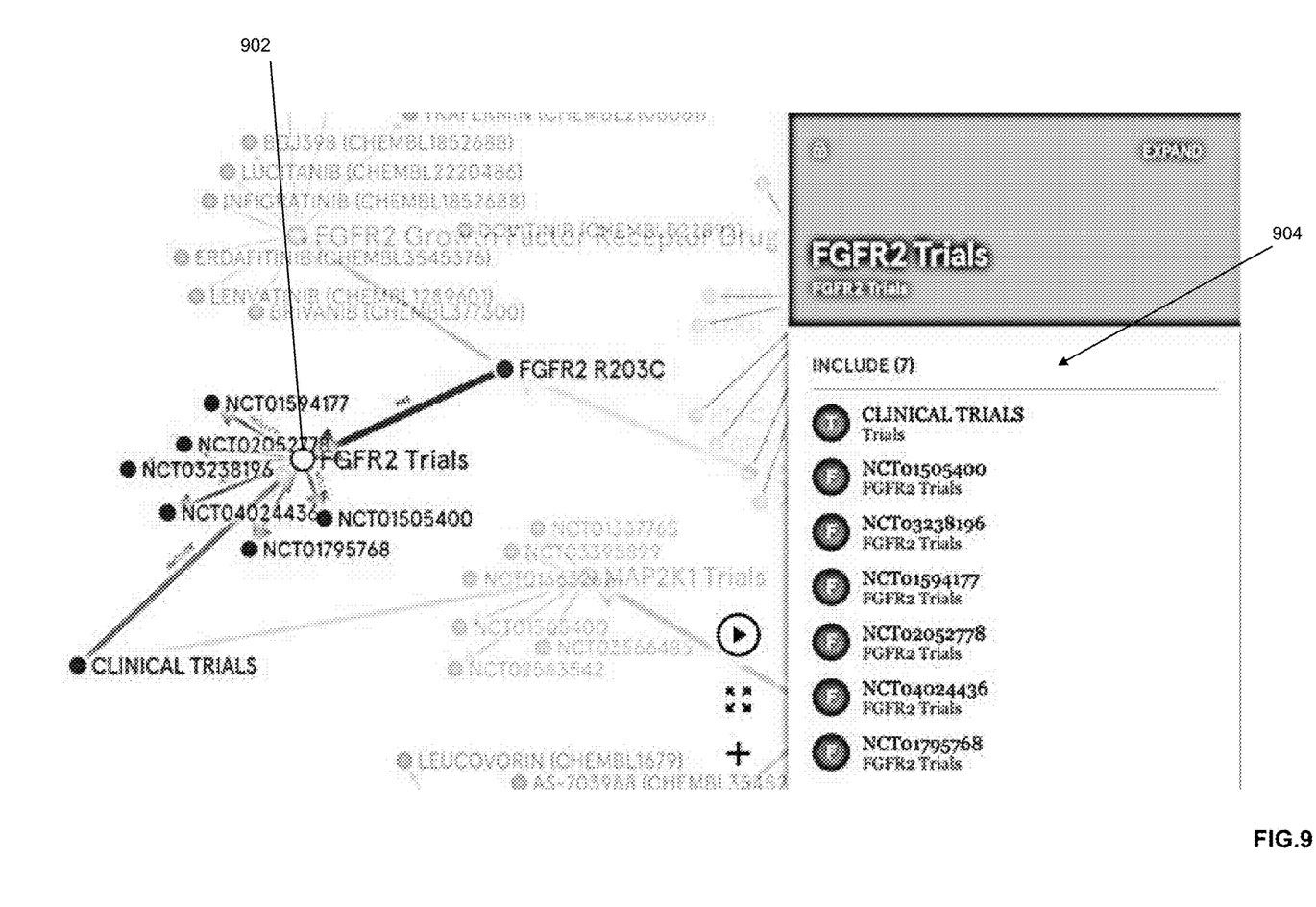
FIG. 9 illustrates another exemplary graphical component of the user interface of FIG. 4.

In addition, graphical components may be used to identify clinical trials relevant to the patient. As shown in FIG. 9, when the FGFR2 R203C gene variant node 902 is clicked, relevant clinical trials 904 are displayed.

Temporal Elements

Referring back to FIG. 4, temporal elements 408 may be configured to display a virtual representation and corresponding information including genomic data, an anatomical feature or pathology taken at different moments in time, potentially including separate episodes of care spanning multiple years.

For example, a user may initiate the retrieval and display of past and present information of the associated genetic variant, anatomical feature or pathology, thereby providing a means of efficiently reviewing and evaluating changes in that genetic variant, feature or pathology over time.

Exemplary Computer System

Figure 10:
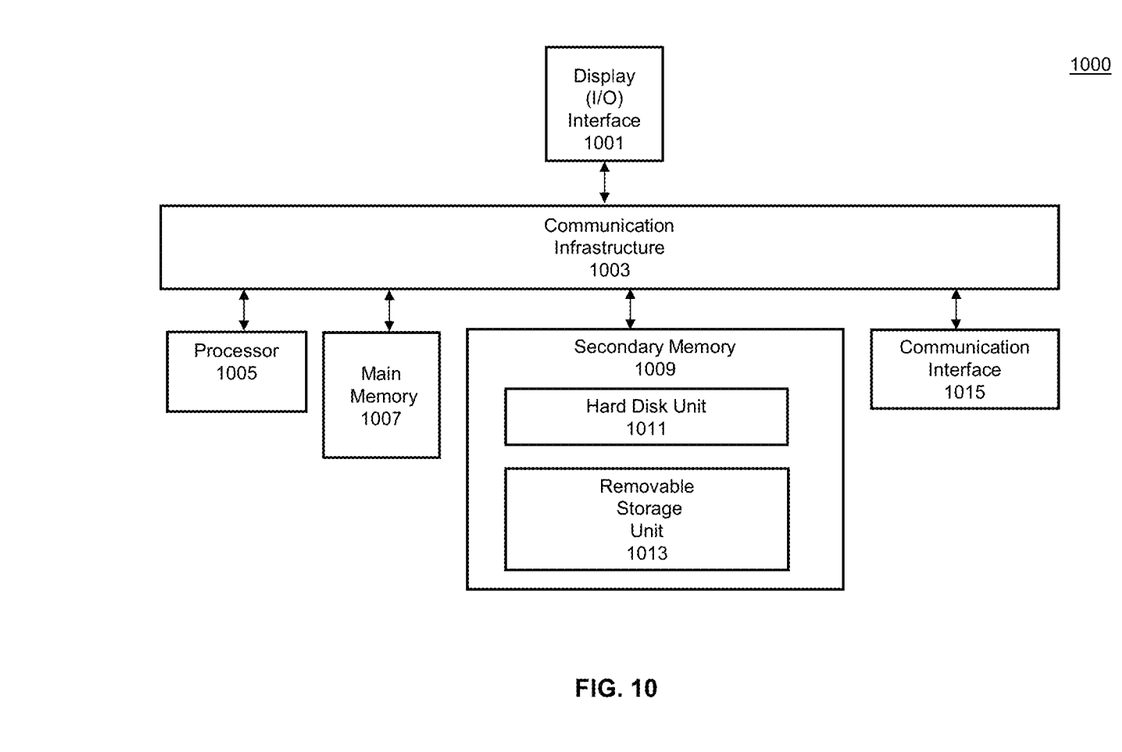
FIG. 10 is an exemplary computing system that may implement all or a portion of the invention.

FIG. 10 illustrates a diagram of a system of which may be an embodiment of the present invention. Computer system 1000 includes an input/output interface 1001 connected to communication infrastructure 1003—such as a bus —, which forwards data such as graphics, text, and information, from the communication infrastructure 1003 or from a frame buffer (not shown) to other components of the computer system 1000. The input/output interface 1001 may be, for example, a display device, a keyboard, touch screen, joystick, trackball, mouse, monitor, speaker, printer, Google Glass® unit, web camera, any other computer peripheral device, or any combination thereof, capable of entering and/or viewing data.

Computer system 1000 includes one or more processors 1005, which may be a special purpose or a general-purpose digital signal processor configured to process certain information. Computer system 1000 also includes a main memory 1007, for example random access memory (RAM), read-only memory (ROM), mass storage device, or combinations of each. Computer system 1000 may also include a secondary memory 1009 such as a hard disk unit 1011, a removable storage unit 1013, or combinations of each. Computer system 1000 may also include a communication interface 1015, for example, a modem, a network interface (such as an Ethernet card or Ethernet cable), a communication port, a PCMCIA slot and card, wired or wireless systems (such as Wi-Fi, Bluetooth, Infrared), local area networks, wide area networks, intranets, etc.

It is contemplated that the main memory 1007, secondary memory 1009, communication interface 1015, or combinations of each, function as a computer usable storage medium, otherwise referred to as a computer readable storage medium, to store and/or access computer software including computer instructions. For example, computer programs or other instructions may be loaded into the computer system 1000 such as through a removable storage device, for example, a floppy disk, ZIP disks, magnetic tape, portable flash drive, optical disk such as a CD or DVD or Blu-ray, Micro-Electro-Mechanical Systems (MEMS), nanotechnological apparatus. Specifically, computer software including computer instructions may be transferred from the removable storage unit 1013 or hard disc unit 1011 to the secondary memory 1009 or through the communication infrastructure 1003 to the main memory 1007 of the computer system 1000.

Communication interface 1015 allows software, instructions and data to be transferred between the computer system 1000 and external devices or external networks. Software, instructions, and/or data transferred by the communication interface 1015 are typically in the form of signals that may be electronic, electromagnetic, optical or other signals capable of being sent and received by the communication interface 1015. Signals may be sent and received using wire or cable, fiber optics, a phone line, a cellular phone link, a Radio Frequency (RF) link, wireless link, or other communication channels. In certain embodiments, data is stored and transmitted according to block chain technology. A block chain may facilitate checking whether data is forged or falsified, by comparing block data (i.e., the medical data) stored in a plurality of node servers to the original data.

Computer programs, when executed, enable the computer system 1000, particularly the processor 1005, to implement the methods of the invention according to computer software including instructions.

The computer system 1000 described may perform any one of, or any combination of, the steps of any of the methods according to the invention. It is also contemplated that the methods according to the invention may be performed automatically.

The computer system 1000 of FIG. 10 is provided only for purposes of illustration, such that the invention is not limited to this specific embodiment. It is appreciated that a person skilled in the relevant art knows how to program and implement the invention using any computer system.

The computer system 1000 may be a handheld device and include any small-sized computer device including, for example, a personal digital assistant (PDA), smart hand-held computing device, cellular telephone, or a laptop or netbook computer, hand held console or MP3 player, tablet, or similar hand held computer device, such as an iPad®, iPad Touch® or iPhone®.

Exemplary Cloud Computing System

Figure 11:
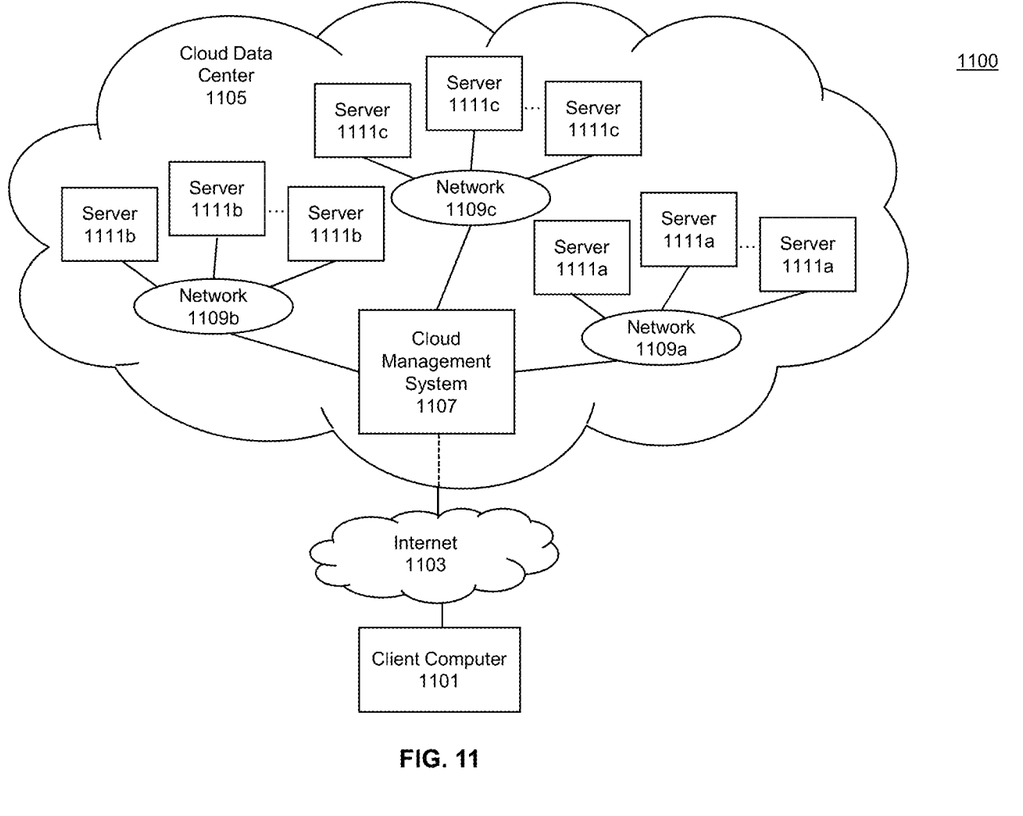
FIG. 11 is an exemplary cloud computing system that may implement all or a portion of the invention.

FIG. 11 illustrates an exemplary cloud computing system 1100 that may be an embodiment of the present invention. The cloud computing system 1100 includes a plurality of interconnected computing environments. The cloud computing system 1100 utilizes the resources from various networks as a collective virtual computer, where the services and applications can run independently from a particular computer or server configuration making hardware less important.

Specifically, the cloud computing system 1100 includes at least one client computer 1101. The client computer 1101 may be any device through the use of which a distributed computing environment may be accessed to perform the methods disclosed herein, for example, a traditional computer, portable computer, mobile phone, personal digital assistant, tablet to name a few. The client computer 1101 includes memory such as random access memory (RAM), read-only memory (ROM), mass storage device, or any combination thereof. The memory functions as a computer usable storage medium, otherwise referred to as a computer readable storage medium, to store and/or access computer software and/or instructions.

The client computer 1101 also includes a communications interface, for example, a modem, a network interface (such as an Ethernet card), a communications port, a PCMCIA slot and card, wired or wireless systems, etc. The communications interface allows communication through transferred signals between the client computer 1101 and external devices including networks such as the Internet 1103 and cloud data center 1105. Communication may be implemented using wireless or wired capability such as cable, fiber optics, a phone line, a cellular phone link, radio waves or other communication channels.

The client computer 1101 establishes communication with the Internet 1103—specifically to one or more servers—to, in turn, establish communication with one or more cloud data centers 1105. A cloud data center 1105 includes one or more networks 1109*a*, 1109*b*, 1109*c* managed through a cloud management system 1107. Each network 1109*a*, 1109*b*, 1109*c* includes resource servers 1111*a*, 1111*b*, 1111*c*, respectively. Servers 1111*a*, 1111*b*, 1111*c* permit access to a collection of computing resources and components that can be invoked to instantiate a virtual machine, process, or other resource for a limited or defined duration. For example, one group of resource servers can host and serve an operating system or components thereof to deliver and instantiate a virtual machine. Another group of resource servers can accept requests to host computing cycles or processor time, to supply a defined level of processing power for a virtual machine. A further group of resource servers can host and serve applications to load on an instantiation of a virtual machine, such as an email client, a browser application, a messaging application, or other applications or software.

The cloud management system 1107 can comprise a dedicated or centralized server and/or other software, hardware, and network tools to communicate with one or more networks 1109*a*, 1109*b*, 1109*c*, such as the Internet or other public or private network, with all sets of resource servers 1111*a*, 1111*b*, 1111*c*. The cloud management system 1107 may be configured to query and identify the computing resources and components managed by the set of resource servers 1111*a*, 1111*b*, 1111*c* needed and available for use in the cloud data center 1105. Specifically, the cloud management system 1107 may be configured to identify the hardware resources and components such as type and amount of processing power, type and amount of memory, type and amount of storage, type and amount of network bandwidth and the like, of the set of resource servers 1111*a*, 1111*b*, 1111*c* needed and available for use in the cloud data center 1105. Likewise, the cloud management system 1107 can be configured to identify the software resources and components, such as type of Operating System (OS), application programs, and the like, of the set of resource servers 1111*a*, 1111*b*, 1111*c* needed and available for use in the cloud data center 1105.

The present invention is also directed to computer products, otherwise referred to as computer program products, to provide software to the cloud computing system 1100. Computer products store software on any computer useable medium, known now or in the future. Such software, when executed, may implement the methods according to certain embodiments of the invention. Examples of computer useable mediums include, but are not limited to, primary storage devices (e.g., any type of random access memory), secondary storage devices (e.g., hard drives, floppy disks, CD ROMs, ZIP disks, tapes, magnetic storage devices, optical storage devices, Micro-Electro-Mechanical Systems (MEMS), nanotechnological storage device, etc.), and communication mediums (e.g., wired and wireless communications networks, local area networks, wide area networks, intranets, etc.). It is to be appreciated that the embodiments described herein may be implemented using software, hardware, firmware, or combinations thereof.

The cloud computing system 1100 of FIG. 11 is provided only for purposes of illustration and does not limit the invention to this specific embodiment. It is appreciated that a person skilled in the relevant art knows how to program and implement the invention using any computer system or network architecture.

While the disclosure is susceptible to various modifications and alternative forms, specific exemplary embodiments of the invention have been shown by way of example in the drawings and have been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

What is claimed is:

1. A computer system for creating a user interface corresponding to a patient medical record, comprising:
   a processor;
   a main memory in communication with the processor via a communication infrastructure, said memory including stored instructions that, when executed by said processor, cause said processor to:
   access a patient medical record including clinical data and genomic data and create a structured data set;
   analyze the structured data set, wherein the structured data set identifies a region of interest corresponding to an anatomical feature and/or pathology;
   generate a user interface corresponding to the patient medical record based on the structured data set, wherein said user interface includes interactive components visually linked to a body map; and
   display the user interface such that a user may interact with the interactive components to retrieve, display or record information corresponding to the patient medical record,
   wherein each interactive component is output as one or more data clusters, each data cluster linked to said medical record and formed by a plurality of nodes extending from a central node, said central node associated with the identified region of interest and at least one of said clinical data and genomic data of the patient medical record, wherein each node extending from said central node corresponds to at least one of a genome, clinical condition, treatment, and clinical trial.

2. The system of claim 1, wherein said body map is a medical image of the region of interest.

3. The system of claim 1, wherein each data cluster is defined by a color or a number corresponding to at least one of a diagnosis, clinical code, and treatment variant.

4. The system of claim 1, wherein selection of each node initiates retrieval and display of information associated with patient specific information.

5. The system of claim 1, wherein each node is selectable and associated with non-personalized reference information relating to at least one of a genome, clinical condition, treatment, and clinical trial.

6. The system of claim 1, wherein said processor is further configured to update said user interface in response to a user input.

7. The system of claim 1, wherein said user interface further includes one or more temporal elements displayed as a series of tabs corresponding to different moments in time of the patient medical record.

8. A method for collecting, displaying, and modeling genomic and clinical data, the method comprising:
accessing a medical record from a database, the medical record including clinical data and genomic data corresponding to a patient;
analyzing the medical record, wherein the clinical data identifies a region of interest and the genomic data provides additional information corresponding to the region of interest;
generate a user interface corresponding to the medical record, wherein said user interface includes interactive components visually linked to a body map;
display, via the user interface, the interactive components such that one or more medical professionals may retrieve, display or record information corresponding to the medical record, wherein each interactive component is output as one or more data clusters, each data cluster linked to said medical record and formed by a plurality of nodes extending from a central node, said central node associated with the identified region of interest and at least one of said clinical data and genomic data wherein each node extending from said central node corresponds to at least one of a genome, clinical condition, treatment, and clinical trial.

9. The method of claim 8, wherein said body map is at least one of an anatomical sketch and a medical image of the region of interest.

10. The method of claim 8, wherein each data cluster is defined by a color or a number corresponding to at least one of a diagnosis, clinical code, and treatment variant.

11. The method of claim 8, wherein selection of each node initiates retrieval and display of information associated with patient specific information of said medical record.

12. The method of claim 8, wherein each node is selectable and associated with non-personalized reference information relating to at least one of a genome, clinical condition, treatment, and clinical trial.

13. The method of claim 8, wherein said user interface is updated in response to a user input.

14. The method of claim 8, wherein said user interface further includes one or more temporal elements displayed as a series of tabs corresponding to different moments in time of the patient medical record.

15. A system for generating a user interface, said system comprising:
one or more processors; and
a memory including instructions that, when executed by the one or more processors, cause the system to:
access a patient medical record including clinical data and genomic data;
create a structured data set, wherein the structured data set identifies a region of interest corresponding to an anatomical feature and/or pathology;
generate a user interface, said user interface comprising:
a body map of the region of interest corresponding to the patient medical record;
a text box including one or more buttons, wherein at least one button corresponds to a process for analyzing clinical data and genomic data based on the patient medical record;
one or more data clusters, each data cluster having a substantially circular shape formed by a plurality of nodes extending from a central node, said central node visually linked to the region of interest and associated with genomic data of the patient medical record, wherein, in response to an input, each node extending from the central node is configured to output information corresponding to at least one of a genome, clinical condition, treatment, and clinical trial; and
a series of selectable tabs configured to augment at least one of the body map, the text box, and the network of nodes according to different moments in time of the patient medical record.

\* \* \* \* \*